United States Patent [19]

Takagi et al.

[11] Patent Number: 4,571,256
[45] Date of Patent: Feb. 18, 1986

[54] NITROGEN FERTILIZER MANIFESTING FUNGICIDAL PROPERTY AGAINST PATHOGENIC FUNGI

[75] Inventors: Shigeki Takagi, Tokyo; Yumiko Urayama, Chigasaki, both of Japan

[73] Assignee: Kabushiki Kaisha Kyoritsu Yuki Kogyo Kenkyusho, Tokyo, Japan

[21] Appl. No.: 734,238

[22] Filed: May 14, 1985

Related U.S. Application Data

[63] Continuation of Ser. No. 442,896, Nov. 19, 1982, abandoned.

[30] Foreign Application Priority Data

Nov. 24, 1981 [JP] Japan ................... 56-186957

[51] Int. Cl.$^4$ ............... E05B 37/06; E05B 37/10; E05B 37/18
[52] U.S. Cl. ................................ 71/28; 71/30
[58] Field of Search ...................... 71/28, 30

[56] References Cited

U.S. PATENT DOCUMENTS

| | | | |
|---|---|---|---|
| 2,467,212 | 4/1949 | Kvalnes | 71/28 |
| 2,652,377 | 9/1953 | Kise | 528/259 |
| 3,112,343 | 11/1963 | Allgeur et al. | 71/28 |
| 3,227,543 | 1/1966 | O'Donnell | 71/28 |
| 3,462,250 | 8/1969 | Justice et al. | 71/28 |
| 3,655,395 | 4/1972 | Karnemaat | 71/28 |
| 3,713,800 | 1/1973 | Karnemaat | 71/28 |
| 3,970,625 | 7/1976 | Moore et al. | 71/28 |
| 4,378,238 | 3/1983 | Goertz | 71/28 |

Primary Examiner—Arthur P. Demers
Attorney, Agent, or Firm—Koda and Androlia

[57] ABSTRACT

A nitrogen fertilizer manifesting fungicidal property against Pathogenic fungi contains as its effective component a water soluble initial condensation product prepared by causing formaldehyde to react with urea. The fertilizer may be admixed with one or more of other fertilizers of various types.

10 Claims, 2 Drawing Figures

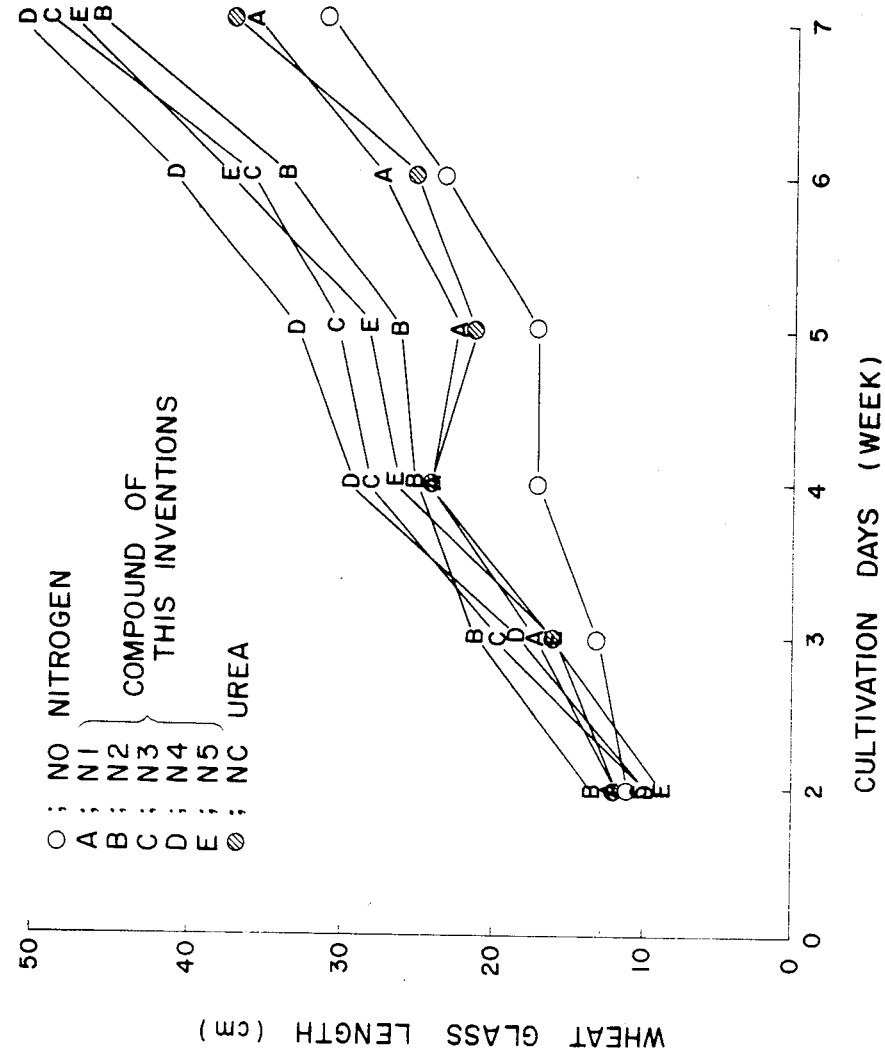

NITROGEN FERTILIZER MANIFESTING FUNGICIDAL PROPERTY AGAINST PATHOGENIC FUNGI

This is a continuation of application Ser. No. 442,896, filed Nov. 19, 1982 now abandoned.

BACKGROUND OF THE INVENTION

This invention relates to nitrogen fertilizer containing as an effective component a water soluble initial condensation product obtained by causing formaldehyde to react with urea and manifesting fungicidal property against Pathogenic fungi.

Such water soluble initial condensation product can be obtained by effecting a reaction between 1 mole of urea and 1-2 moles of formaldehyde in an alkaline or neutral state at normal temperature for 15 minutes to several hours, concentrating an aqueous solution of the reaction product under a reduced pressure and then drying. Among the water soluble initial condensation products are included monomethylolurea, dimethylolurea, 1-methylol-methylene-2 urea, 3-methylolmethylene 2 urea, 1,1'-di-methylol-methylene 2 urea, 1,3'-di-methylolmethylene 2 urea. Pure monomethylolurea and pure dimethylolurea isolated from the initial condensation products or a mixture of monomethylolurea and dimethylolurea have the same fungicidal property as the water soluble initial condensation products.

DESCRIPTION OF THE PRIOR ART

Heretofore, lime nitrogen (calcium cyanamide) has been used as a nitrogen fertilizer having fungicidal property.

Nitrogen contained in lime nitrogen takes the form of a cyanamide so that it is harmful to crops. More particularly, it prevents successful germination or blast or kills roots. Moreover, lime nitrogen applied to soil forms liberated cyanamide due to an action of water, the liberated cyanamide converting into urea by the contact action of mineral materials in the soil. For this reason, when using lime nitrogen for cultivating crops, it is necessary to let it stand until it converts into nonharmful urea. Lime nitrogen is harmful not only to crops but also to human bodies. Thus, when a human being sucks particles of lime nitrogen, injury of respiratory organs and heart would be resulted causing convulsions in an extreme case. As above described, lime nitrogen is a fungicidal fertilizer utilizing harmful property to living things, so that it becomes extremely dangerous depending upon the condition of uses.

SUMMARY OF THE INVENTION

Accordingly, it is an object of this invention to provide a novel nitrogen fertilizer free from poisonous property as lime nitrogen.

Another object of this invention is to provide a novel nitrogen fertilizer which can be prepared at a low cost, harmless and manifests fungicidal property against Pathogenic fungi.

According to this invention, there is provided a nitrogen fertilizer manifesting fungicidal property against Pathogenic fungi, containing as its effective component a water soluble initial condensation product prepared by causing formaldehyde to react with urea.

BRIEF DESCRIPTION OF THE DRAWINGS

In the accompanying drawings:

FIG. 2 is a graph showing the relationship between the length of wheat glass and cultivation days in weeks.

DESCRIPTION OF THE PREFERRED EMBODIMENTS

Figure 1:
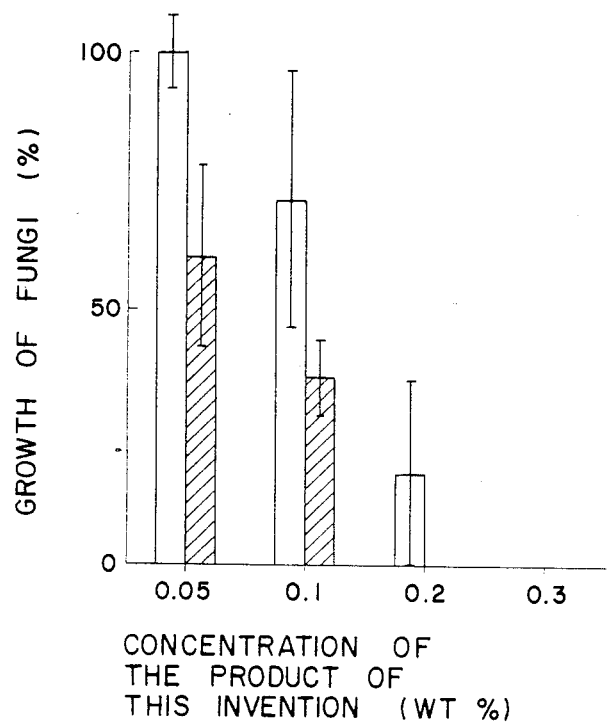
FIG. 1 is a graph showing the fungicidal effect of the compound of this invention upon *Rosellinia necatrix*.

Although the water soluble initial condensation product utilized in this invention per se is not novel, as a result of exhaustive investigation we have found that it manifests excellent fungicidal property against Pathogenic fungi and promotes growth of crops.

In order to prepare water soluble condensation product suitable for use in this invention, it is necessary to carry out the reaction between urea and formaldehyde at a pH higher than 7. When the reaction is carried out at a pH lower than 7, the solubility in water of the product lowers, thereby forming a slow acting nitrogen fertilizer sold under the trade name "Ureaform". The Ureaform is decomposed mainly by microorganisms to be converted into a state that can be absorbed by plants, thus manifesting fertilizer effect. Moreover, no fungicidal function as the water soluble initial condensation product of this invention can be noted in Ureaform.

Even when sulfurous acid hydride or ammonium bicarbonate is incorporated to the water soluble initial condensation product of this invention for the purpose of removing not yet reacted formaldehyde, the novel fungicidal property is not influenced. Further, no adverse effect was noted even when lower alcohols were incorporated for the purpose of preserving the water solubility of the product of this invention over a long time. Although the terminals of methylol radical are alkylated, the fungicidal function of such alkylated compound is the same as that of the product of this invention not incorporated with alcohol. This can be proved by the fact that commercially available methylated methylolurea and methylolurea manifest equivalent effect.

The product of this invention can be used as a soil fungicidal nitrogen fertilizer in various forms and need not always be a pure compound. Liquid in which the reaction has completed can be used as it is. Alternatively, the liquid can be impregnated into such solids as white carbon, diatomaceous earth, brown coal, etc. and then shaped or molded to have desired size and configuration. Where the product of this invention is used for soil in which fungi causes hazard, it is advantageous to use the product of this invention as a pure nitrogen fertilizer, whereas when it is used for preventive purpose it can be used as an ordinary compound fertilizer.

For example, the compound or product of this invention can be admixed with such phosphorus containing fertilizer as superphosphate of lime, fused phosphorous fertilizer, calcined phosphorus fertilizer, serpentine-superphosphate, mixed phosphorus fertilizer (fused phosphorus and multiphosphate); potassium fertilizers such as potassium bicarbonate, potassium sulfate, potassium chloride, and other potassium salt fertilizers, at a ratio of 10:5:5 or 8:8:8. Furthermore, ammonium sulfate, ammonium chloride or urea may be added to the mixture for adjusting the guaranteed quantity of nitrogen content. To the compound fertilizers thus prepared may be added manganese sulfate, calcium carbonate, siliceous fertilizer, calcium hydroxide, lime stone serpentine hydroxide, serpentine carbonate, serpentine sulfate, etc. It is also possible to admix the compound of this invention with conventional compound fertilizer, acidic or basic compound fertilizer, bone meal, fish meal, organic fertilizer, such as vegetable oil cake soil activator, etc.

To have better understanding of this invention the following examples are given.

EXAMPLE 1

Method of Preparing Water Soluble Initial Condensation Product of Urea and Formaldehyde 1.2 g of NaOH was dissolved in 162 g (2 moles) of 37% aqueous solution of formaldehyde. While stirring the mixture, 60 g (1 mole) of urea was dissolved in the mixture. After about 1.5 hours the entire solution was solidified and an aqueous solution of initial condensation product of urea and formaldehyde having a concentration of 54%, a reaction percentage of 96% of formaldehyde and containing 1.14% of not yet reacted formaldehyde was obtained. It was found that this product was completely dissolved in water of 5 times quantity.

In the following Examples 2 and 3 methods of shaping or molding will be described. It should be understood, however, that the type of additives and ratios of admixture are not limited to those described and that parts are weight parts.

EXAMPLE 2

Pure Nitrogen Fertilizer

The water soluble initial condensation product of urea and forlmaldehyde prepared according to Example 1 was molded to have a proper size, for example with an injection molding machine, and then dried to obtain a pure fungicidal fertilizer having a nitrogen content of 8-23%.

EXAMPLE 3

Compound Fertilizer 42 parts of fused phosphorus, 13 parts of KCl, and 5 parts of serpentine carbonate were added to 240 parts of the product prepared according to Example 1 and the mixture was molded with a molding machine to obtain particle fertilizer having a particle size of 15-30 mm.

EXAMPLE 4

Soil Activator

Peat containing an humic acid was used as a carrier. Caltivated products of one or more Bacillus species selected from the group consisting of *Bacillus cereus, Bacillus subtilis,* and *Bacillus megaterium,* and a cultivated product of an Actinomyces selected from the group consisting of *Actinomyces flavoridis, Streptomyces flavus, Streptomyces fradiae,* and *Streptomyces albus* were incorporated into the carrier to form a mixture. 45 parts of this mixture, 10% of the product of example 1, 30 parts of such organic substances as bone meal, fish meal and vegetable oil cake, 5 parts of serpentine carbonate, 45 parts of lime silicate, 5 parts of mixed phosphorus fertilizer, and 0.5 part of crushed mineral containing a minor quantity of necessary elements were admixed together.

The following examples 5, 6 and 7 describe the result of test of the nitrogen fertilizer of this invention.

EXAMPLE 5

The fungicidal effect of dimethylolurea upon *Helicobasidium mompa, Rosellinia necatrix, Fusarium oxsporum, Sclerotinia sclerotiorum, Thanatephorus cucumeris,* and Tricofusarium are shown in the following Table I.

The fungicidal effect was measured in the following manner. Thus, a PDA medium was prepared such that the concentration of the dimethylolurea will be 0–0.05 mole/l and 1 cm fungi disc of each species (or Pathogenic fungi) was inoculated at 25° C. for 3 weeks and the fungicidal effect was measured whether fungi was grown or not. (Only Tricofusarium was inoculated of spore.)

TABLE I

| | Fungicidal effect of dimethylolurea upon each Pathogenic fungi | | | | | | | |
|---|---|---|---|---|---|---|---|---|
| | Growth of Fungi (mm) Concentration (Mole/l) | | | | | | | |
| Pathogenic Fungi | 0 | 0.001 | 0.005 | 0.01 | 0.02 | 0.03 | 0.04 | 0.05 |
| *Helicobasidium mompa* | 85.0 ± 0 | 85.0 ± 0 | 0 | 0 | 0 | 0 | 0 | 0 |
| *Rosellinia necatrix* | 85.0 ± 0 | 85.0 ± 0 | 0 | 0 | 0 | 0 | 0 | 0 |
| *Fusarium oxsporum* | 85.0 ± 0 | 85.0 ± 0 | 85.0 ± 0 | 25.0 ± 15.0 | 0 | 0 | 0 | 0 |
| *Sclerotinia sclerotiorum* | 85.0 ± 0 | 85.0 ± 0 | 0 | 0 | 0 | 0 | 0 | 0 |
| *Thanatephorus cucumeris* | 85.0 ± 0 | 85.0 ± 0 | 85.0 ± 0 | 55.0 ± 18.4 | 55.0 ± 18.4 | 25.0 ± 15.0 | 25.0 ± 15.0 | |
| *Tricofusarium* | 85.0 ± 0 | 85.0 ± 0 | 85.0 ± 0 | 0 | 0 | 0 | 0 | 0 |

EXAMPLE 6

Fungicidal Effect of Methylated Methylolurea upon Pathogenic Fungi

The fungicidal effects of methylated methylolurea upon *Helicobasidium mompa* and *Rosellinia necatrix* are shown in the following Table II.

TABLE II

| | Fungicidal effect of methylated methylolurea upon *Helicobasidium mompa Rosellinia necatrix* | | | | | |
|---|---|---|---|---|---|---|
| Species of Pathogenic fungi | Growth of fungi (mm) Concentration (mole/l) | | | | | |
| | 0 | 0.001 | 0.002 | 0.003 | 0.004 | 0.005 |
| *Helicobasidium mompa* | 73.2 ± 0.9 | 75.1 ± 0.9 | 70.9 ± 0.9 | 63.3 ± 2.2 | 20.0 ± 8.0 | 0 |

TABLE II-continued

Fungicidal effect of methylated methylolurea upon
*Helicobasidium mompa Rosellinia necatrix*

| Species of Pathogenic fungi | Growth of fungi (mm) Concentration (mole/l) | | | | | |
|---|---|---|---|---|---|---|
| | 0 | 0.001 | 0.002 | 0.003 | 0.004 | 0.005 |
| *Rosellinia necatrix* | 85.0 ± 0 | 85.0 ± 0 | 76.2 ± 8.8 | 0 | 0 | 0 |

The fungicidal effect was measured in the following manner. Thus, a PDA medium was prepared such that the concentration of the methylated methylolurea will be 0–0.05 mol/l and 1 cm fungi disc of each species was inoculated at 25° C. for 3 weeks and the fungicidal effect was measured whether fungi was grown or not.

EXAMPLE 7

Fungicidal Effect of the Soil Activator Shown in Example 4 upon *Rosellinia Necatrix*

Barks of twigs of a mulberry tree grown with *Rosellinia necatrix* were peeled off and disposed in the bottom of a tall beaker having a volume of 200 ml. The product prepared in accordance with Example 4 was weighed such that its effective concentration in soil will be 6–0.3%, and then the weighed product was thoroughly admixed with kuroboku soil (black colored surface layer of soil) which was disposed on the barks of mulberry tree in the beaker. In the same manner, samples of soil were prepared to have respective concentrations and 1% of the soil activator according to Example 4 but not containing the product of this invention were tested in the same manner.

All tests were performed with three identical beakers containing identical samples and mean values of the tests were used. The fungicidal effect was measured whether fungi has grown or not. The fungicidal effect is shown in FIG. 1. As can be noted from FIG. 1 the fungicidal effect can be improved by using the soil activator prepared according to Example 3 than using only the product of this invention.

The following Examples 8–11 show cultivation tests utilizing the compound of this invention.

EXAMPLE 8

Comparative Cultivation Tests Using the Compound of this Invention and Urea

We have found that the optimum concentration of urea when cultivating komatsuna (a kind of Chinese cabbage) is about 0.17% (N-800 ppm) where kuroboku soil is used. In this example, the nutritive effect of nitrogen of the compound of this invention was evaluated by taking this nitrogen concentration as a standard.

Tests were carried out by using three 1/500a Wagnel pots and in a green house, and the results of three pots were averaged. The kuroboku soil was dried to form a test soil. Predetermined quantities of the compound of this invention prepared according to Example 2, Na$_2$HPO$_4$, KCl and soil were thoroughly admixed according to the formulation shown in the following Table III. The quantity of water sprinkled was selected to be about 50% of the maximum quantity of the water holding capacity, and 50 seeds of komatsuna were seeded in each pot. Ten days after germination, the seedlings were thinned and remaining 10 seedlings were cultivated for 4 weeks.

The result of caltivation of komatsuna is shown in the following Table IV.

TABLE III

| Test section | Formulation of fertilizer | | | |
|---|---|---|---|---|
| | Nitrogen | | | |
| | Urea | Compound of this invention | Na$_2$HPO$_4$ | KCl |
| N0 | — % | — % | 0.366% | 0.153% |
| N1 | — | 0.021 | 0.366 | 0.153 |
| N2 | — | 0.043 | 0.366 | 0.153 |
| N3 | — | 0.086 | 0.366 | 0.153 |
| N4 | — | 0.171 | 0.366 | 0.153 |
| N5 | — | 0.343 | 0.366 | 0.153 |
| NC | 0.171 | — | 0.366 | 0.153 |

TABLE IV

Comparative cultivation test of komatsuna using compound of this invention and urea

| Test section | Germination (%) | Number of leaves | Length of leaf (mm) | Length of petiole (mm) | Number of individuals alived | Weight of top portion (g) | | Weight of root portion (mg) | |
|---|---|---|---|---|---|---|---|---|---|
| | | | | | | Fresh weight | dry weight | Fresh weight | dry weight |
| N0 | 91 | 3.6 | 6.75 | 6.37 | 30/30 | 3.02 | 0.21 | 173 | 17.2 |
| N1 | 89 | 3.7 | 8.76 | 7.90 | 29/30 | 5.57 | 0.34 | 203 | 22.5 |
| N2 | 95 | 3.7 | 8.62 | 7.32 | 30/30 | 5.90 | 0.33 | 119 | 14.4 |
| N3 | 97 | 3.4 | 8.67 | 7.57 | 30/30 | 6.02 | 0.33 | 95 | 11.1 |
| N4 | 97 | 3.2 | 7.67 | 6.92 | 30/30 | 4.60 | 0.26 | 60 | 7.2 |
| N5 | 81 | 3.3 | 6.75 | 5.67 | 30/30 | 2.81 | 0.16 | 30 | 3.8 |
| NC | 84 | 4.3 | 6.45 | 8.17 | 28/30 | 6.28 | 0.40 | 129 | 14.3 |

In sections utilizing urea, the number of leaves was large, the length of the leaf was long, while the length of the petiole was long. In sections utilizing the compound of this invention, the number of leaves was small, the length of the leaf was long, and the length of the petiole was short.

To realize growth (in terms of weight and leaf length) of plants comparative with that of a case using urea, the required quantity of the product of this invention was found to be in a range of 0.043–0.036% (N-100–200 ppm). When compared with urea, although the nitrogen content of the compound of this invention is only ¼, it has a comparable growth effect upon plants. When compared with a test not applied with nitrogen fertilizer, the compound of this invention is sufficiently effective as a nitrogen containing fertilizer.

EXAMPLE 9

Comparative Cultivation Tests Utilizing the Compound of this Invention and Ammonium Sulfate The nitrogen fertilizer effect of the compound of this invention prepared according to Example 2 was used together with 0.377% of ammonium sulfate (N-800 ppm) based on the optimum concentration of urea determined by the cultivation test of komatsuna described in Example 8.

Cultivation tests were made in the same manner as in Example 8. The soil used was kuroboku soil and it was thoroughly admixed with other ingredients according to the formulation shown in the following Table V. The quantity of water sprinkled was 50% of the maximum quantity of the water holding capacity. 50 seeds of Komatsuna were seeded in each test section. 10 days after germination of the seeds, the seedlings were thinned and remaining 10 seedlings were cultivated for four weeks. The result of cultivation is shown in the following Table VI.

TABLE V

| Test section | Formulation of fertilizer | | | |
|---|---|---|---|---|
| | Nitrogen | | | |
| | $(NH_4)_2SO_4$ | Compound of this invention | $Na_2HPO_4$ | KCl |
| N0 | — % | — % | 0.366% | 0.153% |
| N1 | — | 0.086 | 0.366 | 0.153 |
| N2 | — | 0.171 | 0.366 | 0.153 |
| N3 | — | 0.343 | 0.366 | 0.153 |
| N4 | — | 0.696 | 0.366 | 0.153 |
| N5 | — | 1.374 | 0.366 | 0.153 |
| NC | 0.377 | — | 0.366 | 0.153 |

TABLE VI

Comparative cultivation test of komatsuna using compound of this invention and ammonium sulfate

| Test section | Germination (%) | Blighted seedlings (%) | Number of leaves | Length of leaf (mm) | Length of petiole (mm) | Number of individuals alived | Weight of top portion (g) | | Weight of root portion (mg) | |
|---|---|---|---|---|---|---|---|---|---|---|
| | | | | | | | fresh weight | dry weight | fresh weight | dry weight |
| N0 | 87 | 7.3 | 3.7 | 5.83 | 4.41 | 30/30 | 1.69 | 0.14 | 191.7 | 18.7 |
| N1 | 99 | 0 | 3.1 | 9.10 | 7.50 | 30/30 | 6.22 | 0.31 | 123.3 | 10.6 |
| N2 | 97 | 0 | 3.2 | 8.52 | 5.87 | 30/30 | 4.47 | 0.24 | 80.0 | 5.7 |
| N3 | 89 | 0 | 3.2 | 7.90 | 5.66 | 29/30 | 3.45 | 0.18 | 55.2 | 5.5 |
| N4 | 41 | 0 | 3.2 | 5.83 | 4.50 | 28/30 | 2.02 | 0.11 | 32.1 | 3.1 |
| N5 | 11 | 0 | 3.0 | 5.26 | 3.74 | 21/30 | 1.02 | 0.08 | 21.4 | 3.3 |
| NC | 73 | 20.0 | 5.6 | 9.54 | 8.86 | 29/30 | 6.84 | 0.40 | 113.8 | 12.9 |

In sections applied with ammonium sulfate, the number of the blighted seedlings at the initial stage was large, e.g. 20%. In sections applied with 0.09% of the compound of this invention (N-200 ppm) had equivalent fertilizer effect to the sections applied with ammonium sulfate.

EXAMPLE 10

Cultivation Test of Wheat Using the Compound of this Invention

Cultivation was made similar to Example 8 except outdoor cultivation. Dry kuroboku soil was admixed with predetermined quantities of the compound of this invention of Example 2, $Na_2HPO_4$ and KCl according to the formulation shown in the following Table VII. The quantity of the water sprinkled was selected to be about 50% of the maximum quantity of water holding capacity, and 25 wheat seeds (Norin No. 55) were seeded in each section. 10 days after seeding the seedlings were thinned to leave 27. After four weeks, the seedlings were again thinned and remaining 23 seedlings were cultivated for 12 weeks.

As the quantity of use of the compound of this invention increases the growth of the wheat increases. Furthermore, as shown in the following Table VIII, the number of tillers per stump, the number of ears, the weight of a ear, and the number of harvested seeds increase.

TABLE VII

| Test section | Formulation of fertilizer | | | |
|---|---|---|---|---|
| | Nitrogen | | | |
| | Urea | Compound of this invention | $Na_2HPO_4$ | KCl |
| N0 | — % | — % | 0.366% | 0.153% |
| N1 | — | 0.021 | 0.366 | 0.153 |
| N2 | — | 0.043 | 0.366 | 0.153 |
| N3 | — | 0.086 | 0.366 | 0.153 |
| N4 | — | 0.171 | 0.366 | 0.153 |
| N5 | — | 0.343 | 0.366 | 0.153 |
| NC | 0.086 | — | 0.366 | 0.153 |

TABLE VIII

Fertilizer effect as N of the compound of this invention in the cultivation of wheat

| Test section | Germination (%) | Number of tillers after cultivation for 6 weeks per stump | Analysis at the time of harvest | | |
|---|---|---|---|---|---|
| | | | Number of ears per 9 stumps | ear weight (g)/9 stumps | Weight of seeds (g)/9 stumps |
| N0 | 95 | 2.1 | 10 | 4.48 | 2.3 |
| N1 | 95 | 4.0 | 12 | 10.33 | 4.2 |
| N2 | 97 | 5.6 | 18 | 16.50 | 8.9 |
| N3 | 95 | 7.0 | 25 | 34.33 | 14.8 |
| N4 | 93 | 8.9 | 40 | 61.50 | 30.7 |
| N5 | 73 | 9.8 | 54 | 68.60 | 28.6 |
| NC | 95 | 6.4 | 25 | 37.16 | 13.1 |

As can be noted from these Tables, it was confirmed that the compound of this invention has an efficient fertilizer effect as nitrogen. In test section N5, the weight of the seeds is slightly smaller than test section N4. This is caused by the fact that the wheat was harvested at a time when the seeds have not yet completely ripen.

Comparing test section N4 utilizing the compound of this invention having a concentration of N of 400 ppm with a section NC utilizing urea, it can be noted that the number of tillers, the number of ears, and the weight of seeds are all larger when the compound of this invention is used. Especially, it is remarkable that the weight of seeds has increased by 22.3 times over test section E which proves that the compound of this invention is an excellent nitrogen fertilizer.

EXAMPLE 11

Cultivation with Methylated Methylolurea

The fertilizer effect of methylated methylolurea on the growth of plants was investigated in the same manner. The formulation of the fertilizer is shown in Table IX while the result of cultivation test is shown in Table X.

TABLE IX

| Test section | Fertilizer formulation | | | |
| --- | --- | --- | --- | --- |
| | Nitrogen | | | |
| | Urea | Methylated methylolurea | $Na_2HPO_4$ | KCl |
| N0 | —% | —% | 0.366% | 0.153% |
| N1 | — | 0.026 | 0.366 | 0.153 |
| N2 | — | 0.053 | 0.366 | 0.153 |
| N3 | — | 0.106 | 0.366 | 0.153 |
| N4 | — | 0.211 | 0.366 | 0.153 |
| N5 | — | 0.423 | 0.366 | 0.153 |
| NC | 0.171 | — | 0.366 | 0.153 |

TABLE X

Result of cultivation of komatsuna utilizing methylated methylolurea

| Test section | Germination (%) | Weight of top portion (g) | | Weight of root portion (mg) | |
| --- | --- | --- | --- | --- | --- |
| | | Fresh weight | Dry weight | Fresh weight | Dry weight |
| N0 | 93 | 2.54 | 0.19 | 175.6 | 18.1 |
| N1 | 97 | 5.64 | 0.30 | 158.1 | 15.8 |
| N2 | 95 | 4.58 | 0.26 | 125.7 | 13.3 |
| N3 | 96 | 3.95 | 0.21 | 68.3 | 6.5 |
| N4 | 85 | 2.65 | 0.15 | 41.4 | 3.8 |
| N5 | 78 | 1.93 | 0.11 | 23.4 | 3.4 |
| NC | 83 | 6.52 | 0.39 | 101.7 | 13.3 |

As can be noted from Table X, it was found that methylated methylolurea had an excellent fertilizer effect.

It is believed that the water soluble initial condensation product of this invention can manifest excellent fertilizer effect because it also has Pathogenic fungicidal property. Any soil and composition contain much Pathogenic fungi having a tendency of preventing growth of plants. The water soluble initial condensation product of this invention not only kills harmful Pathogenic fungi but also functions as an efficient nitrogen fertilizer so that when the fertilizer of this invention is used, growth of plants can be accelerated thus increasing harvest.

We claim:

1. A method of supplying fertilizer to plants comprising the steps of:

preparing aqueous solution of nitrogen fertilizer manifesting fungicidal property against pathogenic fungi and containing as its effective component a water soluble initial condensation product containing methylol radicals and prepared by causing formaldehyde to react with urea at a PH higher than 7, said aqueous solution containing said nitrogen fertilizer in an amount of 0.043–0.036%, and applying said aqueous solution to plants.

2. The method according to claim 1 wherein said nitrogen fertilizer further contains sulfurous acid hydride.

3. The method according to claim 1 wherein said nitrogen fertilizer further contains ammonium bicarbonate.

4. The method according to claim 1 wherein said nitrogen fertilizer is admixed with one or more other types of fertilizers.

5. A method of supplying fertilizer to plants comprising the steps of:

preparing aqueous solution of nitrogen fertilizer manifesting fungicidal property against pathogenic fungi and containing as its effective component a water soluble initial condensation product containing methylol radicals and prepared by causing formaldehyde to react with urea at a pH higher than 7;

impregnating said aqueous solution into solid substance selected from the group consisting of white carbon, diatomaceous earth and brown coal;

shaping the impregnated solid substance to have a desired size and configuration, and applying said shaped solid to plants.

6. The method according to claim 5 wherein said nitrogen fertilizer further contains sulfurous acid hydride.

7. The method according to claim 5 wherein said nitrogen fertilizer further contains ammonium bicarbonate.

8. The method according to claim 5 wherein said nitrogen fertilizer is admixed with one or more other types of fertilizers.

9. The method according to claim 1 wherein said pathogenic fungi is one selected from the group consisting of *Helicobasidium mompa, Rosellinia necatrix, Fusarium oxsporum, Sclerotinia sclerotiorum, Thanatephorous cucumeris* and Tricofusarium.

10. The method acccording to claim 5, wherein said pathogenic fungi is one selected from the group consisting of *Helicobasidium mompa, Rosellinia necatrix, Fusarium oxsporum, Sclerotinia sclerotiorum, Thanatephorus cucumeris* and Triocofusarium.

* * * * *